United States Patent
Shi et al.

(10) Patent No.: US 9,701,624 B2
(45) Date of Patent: Jul. 11, 2017

(54) METHOD FOR PREPARING BIURET POLYISOCYANATE

(71) Applicant: Wanhua Chemical Group Co., Ltd., Yantai (CN)

(72) Inventors: Bin Shi, Yantai (CN); Yonghua Shang, Yantai (CN); Haijun Li, Yantai (CN); Weiqi Hua, Yantai (CN); Yuan Li, Yantai (CN); Ensen Ma, Yantai (CN); Biao Wang, Yantai (CN)

(73) Assignee: Wanhua Chemical Group Co., Ltd. (CN)

( * ) Notice: Subject to any disclaimer, the term of this patent is extended or adjusted under 35 U.S.C. 154(b) by 0 days.

(21) Appl. No.: 15/104,338

(22) PCT Filed: Apr. 15, 2014

(86) PCT No.: PCT/CN2014/075379
§ 371 (c)(1),
(2) Date: Jun. 14, 2016

(87) PCT Pub. No.: WO2015/089962
PCT Pub. Date: Jun. 25, 2015

(65) Prior Publication Data
US 2016/0311765 A1  Oct. 27, 2016

(30) Foreign Application Priority Data
Dec. 20, 2013  (CN) .......................... 2013 1 0711542

(51) Int. Cl.
C07C 273/00  (2006.01)
C07C 275/00  (2006.01)
C07C 273/18  (2006.01)

(52) U.S. Cl.
CPC ............................. C07C 273/1872 (2013.01)

(58) Field of Classification Search
CPC .......................... C07C 273/1872; C07C 275/62
See application file for complete search history.

(56) References Cited

U.S. PATENT DOCUMENTS

| 4,028,392 A | 6/1977 | Ogawa et al. |
| 6,066,759 A | 5/2000 | Heider et al. |
| 2009/0292098 A1* | 11/2009 | Wagner ............ C07C 273/1863 528/48 |

FOREIGN PATENT DOCUMENTS

| CN | 101072805 A | 11/2007 |
| CN | 101475680 A | 7/2009 |
| CN | 103709076 A | 4/2014 |
| DE | 1101394 B | 3/1961 |
| DE | 2918739 A1 | 11/1980 |
| DE | 4443885 A1 | 6/1996 |
| EP | 0259233 A2 | 3/1988 |

OTHER PUBLICATIONS

International Search Report for Application No. PCT/CN2014/075379 dated Dec. 20, 2013. (English translation at end of document.).
J. Prakt. Chem, 336, 1994, 185-200.

* cited by examiner

*Primary Examiner* — Yevegeny Valenrod
*Assistant Examiner* — Blaine G Doletski
(74) *Attorney, Agent, or Firm* — Lerner, David, Littenberg, Krumholz & Mentlik, LLP

(57) ABSTRACT

A method for continuously preparing biuret polyisocyanate, comprising: a mixed solution of a diisocyanate and a catalyst with water vapour, in an aerosol form, are continuously reacted in a first reactor; the product obtained therefrom is brought into a second reactor for a further reaction; a tail gas from the second reactor is condensed and refluxed, and the non-condensable gas is brought into a tail gas treatment system; a reaction liquid obtained in the second reactor is further reacted in a third reactor; and then separation is performed for removing monomers, so as to obtain biuret polyisocyanate.

20 Claims, No Drawings

METHOD FOR PREPARING BIURET POLYISOCYANATE

CROSS-REFERENCE TO RELATED APPLICATIONS

The present application is a national phase entry under 35 U.S.C §371 of International Application No. PCT/CN2014/075379 filed Apr. 15, 2014, which claims priority from Chinese Application No. 201310711542.5 filed Dec. 20, 2013, all of which are hereby incorporated herein by reference.

FIELD OF THE INVENTION

The present invention relates to a method for preparing biuret polyisocyanate.

BACKGROUND OF THE INVENTION

Biuret polyisocyanate is widely used in the production of coatings, adhesives, sealants, waterproofing agents, foams, elastomers, fiber processing agents and so on. The preparation method of the aliphatic polyisocyanates having biuret structures has been disclosed in the patent document DE 1101394B published in 1958. Other possible preparation methods are disclosed in the review paper "The synthesis of Aliphatic Polyisocyanates Containing Biuret, isocyanurate or uretdione backbones for use in coating", J.prakt. Chem, 336, 1994, 185-200, and the advantages and drawbacks of these methods are discussed in the review paper.

The preparation methods of biuret polyisocyanate can be mainly divided into two categories: the first is a water method, in which urea is produced by the reaction of diisocyanate and excess water or water donors (for example tertiary monoalcohols, formic acid, crystalline hydrate etc.) and carbon dioxide is produced simultaneously, then biuret polyisocyanate is produced by the reaction of urea and excess diisocyanate; the second is a diisocyanate/diamine method, in which urea is produced directly by diisocyanate and insufficient amount of amine (for example primary amine and/or secondary amine), then biuret polyisocyanate is produced by the reaction of urea and excess diisocyanate. As stated in the above mentioned review paper (J.prakt. Chem, 336, 1994, 185-200), a variety of modifications of the above two methods have been developed and described.

Biuret polyisocyanates prepared by the water method have great monomer stability, i.e. they are hard to break into free diisocyanates, and good tolerance of dilution, i.e. the solution formed by said biuret polyisocyanates and diluents are not likely to be cloudy and generate sediments; and the condition of the preparation process of the water method is relatively mild, and the color number of the obtained products is relative low, thus the method is widely used in manufacturing.

However, in the preparation of the water method, solid state polyurea is very likely to be produced during the reaction process because of the poor compatibility and the insufficient contact of liquid water and diisocyanates; furthermore, the tail gas produced during the reaction still contains a certain amount of diisocyanates and water vapour, and the water vapour can be reacted with a part of diisocyanate gas, solid state polyurea is also easily produced by such reaction, resulting in the blocking of condensers and exhaust pipes and a loss of a part of diisocyanate materials; when solvents are used in the preparation method, polyurea in the condensate of the tail gas will be condensed and refluxed to the products with the solvents. Thus the products will contain polyurea, which will result in poor homogeneity, high cloudiness and white appearance of the products, thus influencing the property of the products, for example the anti-corrosion of the coatings prepared by such products and so on.

In the US patent document U.S. Pat. No. 4,028,392A, it is disclosed that in the presence of hydrophilic organic solvents such as trialkyl phosphate and ethylene glycol methyl ether acetate, diisocyanate is reacted with water to produce biuret polyisocyanates. In European patent document EP0259233A, it is disclosed that in the presence of at least one carboxylic acid and/or carboxylic acid anhydride as catalysts, diisocyanate is reacted with water; in said method, it is also disclosed that methyl phosphate and/or ethyl phosphate and alkoxyl alkyl carboxylate can be used simultaneously as solubilizers, to increase the solubility of water in the solution of diisocyanate and the catalyst. In the above two preparation methods, due to the use of a necessary amount of solvents or solvent mixtures, a relative low biuret polyisocyanate space-time yield is obtained compared with the condition that no solvents are used, and the polyurea produced in a tail gas is condensed and refluxed to the products with solvents, resulting in a cloudy product with white appearance obtained after separation. Moreover, devices and energy-consumption are increased and a more complex operation is required due to the use of solvents, thus more complex distillation operation is required to separate solvents.

In German patent document DE2918739A1, it is disclosed a method for preparing polyisocyanate having biuret structure by the reaction of hexamethylene diisocyanate (HDI) and water, wherein water is mixed with air and/or inert gas in the form of vapour and then is added to the mixed solution of HDI and a catalyst with the temperature of 110-130° C., the reaction is carried out under 150-170° C. The drawback of said method is, as a single reactor is used for the operation of mixing of gas and liquid, the conversion rate of water vapour is not high enough, the tail gas generated during the reaction process produce a large amount of solid polyurea, resulting in the blocking of the device parts, especially the tail gas pipes; meanwhile, the tail gas is not treated, resulting in a great loss of diisocyanate materials.

In the Chinese patent document CN101475680A, it is disclosed a method of synthesizing hexamethylene diisocyanate biuret by spraying, wherein biuret polyiscyanate is prepared by the reaction of hexamethylene diisocyanate and water that is in the form of fogdrop achieved by the use of high pressure. As water cannot be dispersed timely and sufficiently when liquid drop-like water is reacted with hexamethylene diisocyanate, polyurea is formed unavoidably, thus resulting in highly cloudy products with white appearance obtained after separation.

In the Chinese patent document CN101072805A, it is disclosed a method for preparing a storage-stable colorless polyisocyanates having biuret groups. A single reactor is used in said method, and water participated in the reaction is in the form of water vapour to solve the problem of water dispersing. Meanwhile, cold hexamethylene diisocyanate is used to wash tail gas, thus decreasing the loss of the material, hexamethylene diisocyanate. However, as a single reactor is used in operation in said method, the conversion rate of water is not high enough, resulting in a large amount of water left in the returning condensate, these water are reacted with diisocyanate to produce polyurea, leading to products with high cloudiness obtained after separation.

Because the current biuret polyisocyanate preparation methods have many drawbacks, a new biuret polyisocyanate preparation method that will not cause the blocking of the exhaust pipes of condensers during the reaction process and has a low diisocyanate material loss and will produce products with low cloudiness and transparent appearance is required.

SUMMARY OF THE INVENTION

The present invention aims at overcoming the drawbacks of the prior art technology, and providing a method of producing biuret polyisocyanate that does not cause the blocking of the exhaust pipes of condensers, and has a low diisocyanate material loss and obtains products with low cloudiness, transparent appearance and great application performances.

In order to achieve the above purpose, the present invention adopt the following technical solutions:

A method for continuously preparing biuret polyisocyanate, comprising:

a) a mixed solution of a diisocyanate and a catalyst, and water vapour, in an aerosol form, are continuously reacted in a first reactor; wherein the continuous phase of the aerosol is the water vapour, the dispersed phase is the mixed solution of the diisocyanate and the catalyst;

b) the product obtained in step a) is brought into a second reactor for a further reaction; a tail gas from the second reactor is condensed and refluxed, and the non-condensable gas is brought into a tail gas treatment system;

c) the reaction liquid obtained in step b) is further reacted in a third reactor;

d) a separation of the reaction liquid obtained in step c) is performed for removing monomers, so as to obtain biuret polyisocyanate.

In the method of the present invention, said diisocyanate is an aliphatic and/or alicyclic diisocyanate, and/or aromatic diisocyanate, i.e. said diisocyanate can be any one of aliphatic, alicyclic or aromatic diisocyanates or the combination thereof.

Said alicyclic diisocyanate is a diisocyanate comprising at least one alicyclic ring system.

Said aliphatic diisocycante is a diisocyanate that only comprises straight-chains or branched chains, i.e. compounds without rings, i.e. a diisocyanate without ring structure.

Suitable diisocyanates are preferably aliphatic and/or alicyclic diioscyanates with 4-20 carbon atoms, or diphenylmethane diisocyanate or toluene diisocyanate.

One or two or more of tetramethylene diisocyanate, hexamethylene diisocyanate (HDI), octamethylene diiscoyanate, decamethylene diisocyanate, dodecamethylene diisocyanate, tetradecamethylene diisocyanate, derivatives of lysine diisocyanate, tetramethylbenzene dimethylene diisocyanate, 4,4'- or 2,4'-di(cyclohexyl isocyanate)methane ($H_{12}$MDI) and 3-isocyanatomethyl-3,5,5,-trimethylcyclohexy isocyanate (isophorone diisocyanate) are more preferred, one or two or more of HDI, $H_{12}$MDI and isophorone diisocyanate are especially preferred.

In the method of the present invention, the reaction is carried out preferably under the presence of at least one catalyst.

Said catalyst can be the OH-acidic compound such as disclosed in the German patent document DE4443885A1. The advantages of these catalysts are their low volatility and thus can be filtered out as salts from reaction mixtures or can be kept in the final products as noninterfering compounds. Another advantage of these compounds is the great catalytic activity of the acids. The OH-acidic compounds that are suitable for the present invention are especially Brnsted acids. Said OH-acidic compounds can be preferably chosen among the following compounds, one or mixtures of more of phosphoric acid, monoalkyl phosphate, dialkyl phosphate, monoaryl phosphate, diaryl phosphate, monocarboxylic acid and dicarboxylic acid. Preferably, said monoalkyl phosphate, dialkyl phosphate, monoaryl phosphate or diaryl phosphate are the aliphatic, branched aliphatic or araliphatic groups there of with 1-30, preferably 4-20 carbon atoms, for example, methyl phosphate, ethyl phosphate, dibutyl phosphate, dihexyl phosphate, 2-ethyl hexyl phosphate, isooctyl phosphate, n-dodecyl phosphate, diethyl phosphate, di-n-propyl phophsate, di-n-butyl phosphate, diisoamyl phosphate, di-n-decyl phosphate, diphenyl phosphate and mixtures thereof. Suitable monocarboxylic acids and dicarboxylic acids are, for example formic acid, acetic acid, propionic acid, butyric acid, neopentanoic acid, stearic acid, naphthenic acid, oxalic acid, malonic acid, succinic acid, adipic acid, benzoic acid, phthalic acid etc. and mixtures thereof. One or two of dibutyl phosphate and propionic acid are more preferred.

The amount of said catalyst is 0.1-3.0 wt % based on the total amount of the used diisocyanates, the catalysts can be added to the diisocyanates after being dissolved by suitable solvents or after being dispersed or can be added directly to the diisocyanates. It is preferred to add the catalyst directly to the diisocyanates.

In the method of the present invention, the continuous phase of the aerosol form is the water vapour, the dispersed phase is the mixed solution of the diisocyanate and the catalyst. The droplet size of the dispersed phase in the aerosol form is 0.01-50 μm, preferably 0.5-20 μm, especially preferably 1-5 μm. Said aerosol can be prepared by a mechanical spraying device or an ultrasonic dispersing device.

It is required for the dispersed phase of the aerosol to possess droplet size that are relatively small and a uniform droplet size distribution, the smaller the droplet size is, the higher the energy of dispersion is required. Too small droplet size is not suitable from an economical prospect; but too large droplet size will cause an unstable colloid, and the specific surface of the liquid droplet will be smaller, the conversion rate of the water vapour will be lower. Upon repeated experiments, it is discovered by the inventor that, within the droplet size range provided in the present invention, the aerosol is relatively stable, and the conversion rate of the water vapour is high and the consumption of energy is relatively low.

It is suitable to preheat the mixed solution of the diisocyanate and the catalyst to the temperature of 100-160° C. before the formation of the aerosol.

Preferably, the temperature of the water vapour used to form the aerosol is 100-160° C.

In order to ensure the stability of the prepared aerosol, preferably, the difference of the temperature of the mixed solution of the diisocyanate and the catalyst and the temperature of the water vapour is no more than 10° C., preferably no more than 2° C.

In the method of the present invention, the molar ratio of the diisocyanate and the water vapour is 3:1-15:1, preferably 5:1-12:1.

In the method of the present invention, the water vapour can form an aerosol with the mixed solution of the diisocyanate and the catalyst directly to carry out a reaction; it is also possible to dilute the water vapour by an inert gas then allow the diluted water vapour to form aerosol to carry out a reaction. Preferably, the water vapour is not diluted by inert gas but is reacted directly.

When water vapour is diluted by an inert gas, the continuous phase of the aerosol formed in step a) is the mixed gas of the water vapour and the inert gas. Said inert gas should not be reacted with diisocyanate and the catalyst under reaction condition. Said inert gas is for example carbon dioxide, carbon monoxide, nitrogen, helium, argon, hydrocarbons such as methane and so on and mixtures thereof, preferably carbon dioxide and/or nitrogen, especially preferably nitrogen.

The molar ratio of said inert gas and the water vapour is 0:100-1:0.1, especially preferably 0:20-1:1, more preferably 0-1000:100, more preferably 0-100:100.

Solvents cannot be added or can be added to the mixed solution of the diisocyanate and the catalyst for dilution.

Preferably, no solvents are added to the mixed solution of the diisocyanate and the catalyst for dilution.

When solvents are added to the mixed solution of the diisocyanate and the catalyst, the dispersed phase of the aerosol formed in step a) is the mixed solution of the diisocyanate, the catalyst and the solvents. Suitable solvents are for example: butyl acetate, ethyl acetate, tetrahydrofuran, propylene glycol methyl ether acetate, dimethylbenzene, propylene glycol diacetate, butanone, methyl isoamyl ketone, cyclohexanone, hexane, toluene, dimethylbenzene, benzene, chlorobenzene, o-dichlorobenzene, hydrocarbon mixtures, dichloromethane and/or trialkyl phosphate, preferably propylene glycol methyl ether acetate, triethylphosphate, tri-n-butyl phosphate, trimethyl phophate and or mixtures of these compounds in any proportion. Solvents are selected to be added to somehow inhibit the formation of polyurea, meanwhile, adding solvents will decrease the space-time yield of the reaction.

Preferably , no solvents are added to the mixed solution of the diisocyanate and the catalyst in the method of the present invention.

In the method of the present invention, the conversion rate of water vapour in the first reactor is 80-95%, preferably 85-92%, based on the water vapour enter into the first reactor.

More preferably, the total conversion rate of water vapour after step b) is larger than 95%, preferably larger than 99%, based on the water vapour enter into the first reactor.

It is revealed by studying that it is only when the conversion rate of the water vapour in the first reactor is larger than 80%, the total conversion rate of the water vapour of the second reactor can be guaranteed to be larger or equal to 95%; when the conversion rate of the first reactor is larger than 95%, the volume of the reaction device will increase dramatically, too large device will result in a huge investment and the device will be difficult to be processed. The total conversion rate of the second reactor can be guaranteed to be above 95% or even above 99% by strictly controlling the conversion rate of water vapour of the first reactor. Because of the high conversion rate of water vapour, there's very little water in the second reactor after condensation, thus there's little chance for the liquid water to form polyurea with diisocyanate, there's no solid polyurea or very little polyurea formed in the condenser tube, thus solving the problem of the blocking by polyurea in condenser tubes and tail gas exhaust pipes, which greatly decrease the frequency of cleaning the pipes; diisocyanate gas will not react or will seldom be reacted to form polyurea and will return to the second reactor after condensation, thus the loss rate is very low; the polyurea content in the biuret polyisocyanate products obtained finally is very low, allowing to produce products with great homogeneity, high gloss and transparent appearance, when used to prepare coatings, the prepared coatings will have very excellent performances such as anti-corrosion.

During the preparation process, the conversion rate of water vapour can be adjusted comprehensively by the temperature and pressure of the first and the second reactor and the residence time of the aerosol in the first and the second reactor. The conversion rate of water vapour can be determined by extracting the aerosol in the first reactor, measuring the content of carbon dioxide in said reactor and then converting the measurement.

Preferably, the residence time of aerosol in the first reactor is 10-60 min, preferably 20-40 min.

In the method of the present invention, the absolute pressure in the first reactor is 0.1-1 Mpa, preferably 0.11-0.15 Mpa, the temperature in the reactor is 100-160° C. When the above pressure and temperature are used, the conversion rate of water vapour in the first reactor can be guaranteed within the above suitable range.

As the device for the reaction of the aerosol formed by the mixed solution of the diisocyanate and the catalyst and the water vapour, said first reactor can be a vertical tubular reactor, a tower reactor or a tank reactor with high height-to-diameter ratio, preferably a tower reactor.

In one embodiment of the present invention, said first reactor can be a device group composed of two or more of the above reactors that are vertically connected in series.

After the reaction of the aerosol formed by the mixed solution of the diisocyanate and the catalyst and water vapour in the first reactor, the obtained reaction mixture is still in the form of aerosol, said reaction mixture can be provided from the top or bottom of the first reactor, preferably from the top of the first reactor. It's important to note that in "the product obtained in step a) is brought into a second reactor for a further reaction" described in the above step b), the "product" actually means the reaction mixture in the aerosol form that includes the produced biuret polyisocyanate, carbon dioxide, unreacted diisocyanate and water vapour etc., which can be easily understood by those skilled in the art.

The outlet of the first reactor and the inlet of the second reactor can be connected by an insert tube. In order for the mixture in the second reactor to disperse more homogeneously, preferably, the end of the insert tube that is connected to the second reactor is equipped with a porous dispersion device.

The reaction of the aerosol formed by the mixed solution of the diisocyanate and the catalyst and water vapour in the first reactor lasts until the conversion rate of water vapour reaches 80-95%, then the aerosol enters into the second reactor under pressure. On top of the second reactor, it is provided a condensation reflux device and a tail gas exhaust pipe, said tail gas exhaust pipe is connected to the tail gas processing system. Said tail gas processing system can be a solvent-absorbing system or a waste oil- washing system, to absorb the diisocyanate component left in tail gas and thus to avoid pollution in air.

The average residence time of water vapour in the second reactor is 20-200 min, preferably 30-120 min.

The reaction pressure in the second reactor is atmospheric pressure, the temperature of the reactor is 120-160° C.

The reaction carried out in the second reactor is mainly the reaction of the mixed solution of a diisocyanate and a catalyst with water vapour, in the state of aerosol. The separation of gas and liquid is achieved after the reaction, wherein the liquid components are mainly the produced biuret polyisocyanate and the unreacted diisocyanate raw material, and the gas components are mainly the produced carbon dioxide and trace of water vapour and diisocyanate gas.

Suitable reactor for the second reactor can be a tank reactor or a tower reactor, preferably a tank reactor.

Based on the water vapour entered into the first reactor, the total conversion rate of the water vapour in the second reactor is larger than or equal to 95%, preferably the total conversion rate of water vapour is larger than or equal to 99%. The total conversion rate of water vapour can be determined by measuring the carbon dioxide content in tail gas. When the reaction in the second reactor reaches the above conversion rate of water vapour, the liquid mixture in the second reactor is pumped into the third reactor.

It is important to note that in "the reaction liquid obtained in step b) is further reacted in a third reactor" described in the above step c), the "reaction liquid" means the liquid reaction mixture obtained after the reaction in the second reactor.

In the method of the present invention, the reaction temperature of the third reactor is 130-180° C., the reaction pressure is atmospheric pressure, the average residence time is 20-200 min, preferably 60-120 min.

The maturing in the third reactor is mainly the reaction of the produced biuret polyisocyanates with diisocyanate raw materials to produce biuret polyisocyanates with higher functionality. The products produced after maturing have great monomer stability i.e. are unlikely to break into free diisocyanates. The materials and the products in the third reactor are all liquid.

Said third reactor can be a tubular reactor, a tank reactor etc., preferably a tubular reactor. It is revealed that continuously maturing in tubular reactors can significantly improve the stability of the products.

In the method of the present invention, separation devices are used to perform the separation of the reaction liquid obtained in step c) for removing monomers to separate biuret polyisocyanate from the unreacted excess diisocyanate raw materials. Said separation devices can be a film evaporator and/or a short-path evaporator. A two-stage separation device can be used in said step, the separation device for the first stage is preferably a film evaporator, the temperature for the separation of the materials is 130-170° C., the absolute pressure is 50-300 Pa; The separation device for the second stage is preferably a short-path evaporator, the separation temperature of the materials is 140-180° C., the absolute pressure is 5-30 pa. The diisocyanate monomer content in the product obtained by the separation using the above separation devices and conditions can be lower than 0.5 wt %, even lower than 0.3 wt %, the quality of the product is great.

The biuret polyisocyanate product obtained by separation can be diluted by solvents, it can be diluted by one or two of propylene glycol methyl ether acetate, butyl acetate, ethyl acetate, dimethylbenzene, the content of biuret polyisocyanate in the diluted solution is 75±1 wt %.

The "OH-acidic compound" in the present invention is the —OH-containing compounds that can dissociate $H^+$.

The "average residence time" in the present invention is the average time for the reaction materials from entering into the reactor to leaving the reactor.

The "space-time yield" in the present invention is the mass of product obtained in unit time for a unit volume or unit area of reactor device.

The "water vapour conversion rate" or the "conversion rate of water vapour" is the mass ratio of the water vapour participates in the reaction in the reactor and the water vapour enters into the reactor.

The "biuret polyisocyanates" and the " polyisocyanates comprising biuret structures" in the present invention means the same.

Compared with the prior art technology, the advantages of the present invention lie in:

1. The reaction materials in the present invention are mixed and reacted in the form of aerosol, which largely increase the contact area of water vapour and the mixed solution of the diisocyanate and the catalyst, and significantly increase the conversion rate of water vapour, avoiding the problem of forming a large amount of solid polyurea caused by the reaction of liquid water or water vapour with diisocyanate in the prior art technology.

2. In the present invention, the total conversion rate of the water vapour can reach to above 95% by reasonably adjusting the conversion rate of the water vapour in the first and second reactors, which largely decrease the amount of free water or water vapour. When tail gas is condensed through the condenser, there's very little solid polyurea generated in the tail gas exhaust pipe or the condenser, the loss of diisocyanate material is significantly decreased, and the problem of the blocking of the condenser and the tail gas exhaust pipe is solved.

3. The content of solid polyurea is very low in the product, the content of diisocyanate monomer is also very low, the product possess high homogeneity, good gloss, great application performances. Especially when the obtained products are used to prepare coatings, the prepared coatings possess very excellent anti-corrosion property.

DETAILED DESCRIPTION OF THE INVENTION

The present invention will be further illustrated by the following examples, it should be noted that the examples are not the limitations for the extent of protection of the present invention.

The test method of the content of diisocyanate monomers in the examples and the comparative examples:

About 1 g (exact value 0.0001 g) biuret polyisocyanate sample is weighed and placed in 25 ml volumetric flask, about 10 ml dichloromethane is added to dissolve and mix homogeneously, then about 5 ml dibutylamine and two drops of dibutyltin dilaurate are added, and dichloromethane is added until the scale mark of the volumetric flask is tangent with the lowest position of the liquid level. The volumetric flask is placed into oven at 50° C. for 3 hours, then it is taken out and cooled, then dichloromethane is added until the scale mark of the volumetric flask is tangent with the lowest position of the liquid level, after the filtration by 0.45 μm filter membrane, the solution is injected into a liquid chromatograph for analysis, the injection volume is 10 μL. Then a standard curve is made by the corresponding diisocyanate, and the content of monomers is obtained by quantifying with an external-standard calibration curve method.

Liquid chromatographic analysis: Shimadzu LC-20AT, with SIL-20A autosampler, CTO-10AS column incubator, SPD-20A tester, the conditions of chromatography: chromatographic column: Wondasil C18 5 μm (4.6 mm×250 mm), gradient elution: water:methanol=67:33, column temperature 40° C., flow rate: 1.0 ml/min, detection wavelength: 258 nm, quantitative method: external standard method.

EXAMPLE 1

The mixed solution of hexamethylene diisocyanate and the catalyst, dibutyl phosphate was prepared, wherein the amount of dibutyl phosphate was 0.2 wt % of the mass of hexamethylene diisocyanate, said mixed solution was pumped continuously into the preheater for preheating to 155° C.; water vapour was preheated to 155° C. in another preheater, then the mixed solution and the water vapour were added to the device for preparing aerosol, the flow rate of the mixed solution of hexamethylene diisocyaante and the catalyst was 15 kg/h, the feeding rate of water vapour was 0.15 kg/h, the mixed solution and the water vapour were dispersed to prepare aerosol, in the aerosol, the continuous phase was the water vapour, the dispersed phase was the mixed solution of hexamethylene diisocyanate and dibutyl phosphate, the average droplet size in the dispersed phase in the aerosol was 3 µm. The obtained aerosol entered into the first reactor through the top of the first reactor, a vertical tower reactor for a reaction, the pressure in the first reactor was 0.25 MPa, the temperature was 155-160° C., the average residence time of aerosol in the first reactor was 25 min, the conversion rate of the water vapour was 90% (based on the water vapour enter into the first reactor), then the mixture in the aerosol form entered into the second reactor which is a stirring tank reactor from the first reactor through the insert tube. The top of the second reactor was provided a condenser with circulating water for cooling and refluxing. The temperature in the second reactor was 155-160° C., the average residence time of the reaction liquid in the second reactor was 50 min, the total conversion rate of water vapour was 99.5% (based on the water vapour entered into the first reactor). The separation of the gas and the liquid was achieved substantially after the reaction of the reaction mixture in the second reactor, wherein the gas was condensed and refluxed with the condenser, the temperature of the condensed water was 25-35° C., the mixed liquid entered into the third reactor, a tubular reactor. The temperature in the third reactor was 155-160° C., the average residence time of the reaction liquid in the third reactor was 100 min, the obtained reaction liquid was separated by a two-stage film evaporator to remove monomers, the diisocyanate monomers contained were removed to obtain products with 100% solid content of biuret. In the two-stage film evaporator, the separation temperature of the first-stage film evaporator was 130° C., the absolute pressure was 50 pa; the separation temperature of the second film evaporator was 140° C., the absolute pressure was 5 pa, biuret products was obtained by separation. The loss of hexamethylene diisocyanate was 0.11 wt % (based on the hexamethylene diisocyanate added in the first reactor). The content of the diisocyanate monomers in the product was 0.15 wt % (liquid chromatographic analysis, the same as below), the color number was 5# (Pt—Co color), the product was very transparent, and the frequency for cleaning the tail gas pipe was once/12 months.

EXAMPLE 2

The mixed solution of $H_{12}MDI$ and the catalyst, propanoic acid was prepared, wherein the amount of propanoic acid was 1 wt % of the mass of $H_{12}MDI$, said mixed solution was pumped continuously into the preheater for preheating to 130° C.; water vapour was preheated to 130° C. in another preheater, then the mixed solution and the water vapour were added to the device for preparing aerosol, the flow rate of the mixed solution of $H_{12}MDI$ and propanoic acid was 15 kg/h, the feeding rate of water vapour was 0.34 kg/h, the mixed solution and the propanoic acid were dispersed to prepare aerosol, in the aerosol, the continuous phase was the water vapour, the dispersed phase was the mixed solution of $H_{12}MDI$ and propanoic acid, the average droplet size in the dispersed phase in the aerosol was 50 µm. The obtained aerosol entered into the first reactor through the top of the first reactor, a vertical tower reactor for a reaction, the pressure in the first reactor was 0.45 MPa, the temperature was 130-135° C., the average residence time of aerosol in the first reactor was 10 min, the conversion rate of the water vapour was 80% (based on the water vapour enter into the first reactor), then the mixture in the aerosol form entered into the second reactor which is a stirring tank reactor from the first reactor through the insert tube. The top of the second reactor was provided a condenser with circulating water for cooling and refluxing. The temperature in the second reactor was 135-140° C., the average residence time of the reaction liquid in the second reactor was 110 min, the total conversion rate of water vapour was 98.5% (based on the water vapour entered into the first reactor). The separation of the gas and the liquid was achieved substantially after the reaction of the reaction mixture in the second reactor, wherein the gas was condensed and refluxed with the condenser, the temperature of the condensed water was 25-35° C., the mixed liquid entered into the third reactor, a tubular reactor. The temperature in the third reactor was 135-140° C., the average residence time of the reaction liquid in the third reactor was 35 min, the obtained reaction liquid was separated by a two-stage film evaporator to remove monomers, the diisocyanate monomers contained were removed to obtain products with 100% solid content of biuret. In the two-stage film evaporator, the separation temperature of the first-stage film evaporator was 150° C., the absolute pressure was 150 pa; the separation temperature of the second film evaporator was 160° C., the absolute pressure was 25 pa, biuret products was obtained by separation. The loss of $H_{12}MDI$ was 0.15 wt % (based on the $H_{12}MDI$ added in the first reactor). The content of the diisocyanate monomers in the product was 0.35 wt %, the color number was 5# (Pt—Co Color), the product was transparent, and the frequency for cleaning the tail gas pipe was once/5 months.

EXAMPLE 3

The mixed solution of isophorone diisocyanate and the catalyst, dibutyl phosphate was prepared, wherein the amount of dibutyl phosphate was 0.2 wt % of the mass of isophorone diisocyanate, said mixed solution was pumped continuously into the preheater for preheating to 110° C.; water vapour was preheated to 110° C. in another preheater, then the mixed solution and the water vapour were added to the device for preparing aerosol, the flow rates of isophorone diisocyanate and dibutyl phosphate were 15 kg/h, the feeding rate of water vapour was 0.21 kg/h, the mixed solution and the dibutyl phosphate were dispersed to prepare aerosol, in the aerosol, the continuous phase was the water vapour, the dispersed phase was isophorone diisocyanate and dibutyl phosphate, the average droplet size in the dispersed phase in the aerosol was 38 µm. The obtained aerosol entered into the first reactor through the top of the first reactor, a vertical tower reactor for a reaction, the pressure in the first reactor was 0.85 MPa, the temperature was 110-115° C., the average residence time of the aerosol in the first reactor was 40 min, the conversion rate of the water vapour was 92% (based on the water vapour enter into the first reactor), then the mixture in the aerosol form entered into the second reactor which is a stirring tank reactor from the first reactor through the insert tube. The top of the second reactor was provided a condenser with circulating water for cooling and refluxing. The temperature in the second reactor was 120-125° C., the average residence time of the reaction liquid in the second reactor was 30 min, the total conversion rate of water vapour was 95.5% (based on the water vapour entered into the first reactor). The separation of the gas and the liquid was achieved substantially after the reaction of the reaction mixture in the second reactor, wherein the gas was condensed and refluxed with the condenser, the temperature of the condensed water was 25-35° C., the mixed liquid entered into the third reactor, a tubular reactor. The temperature in the third reactor was 130-135° C., the average residence time of the reaction liquid in the third reactor was 180 min, the obtained reaction liquid was separated by a two-stage film evaporator to remove monomers, the diisocyanate monomers contained were removed to obtain products with 100% solid content of biuret. In the two-stage film evaporator, the separation temperature of the first-stage film evaporator was 170° C., the absolute pressure was 300 pa; the separation temperature of the second film evaporator was 180° C., the absolute pressure was 30 pa, biuret products was obtained by separation. The loss of isophorone diisocyanate was 0.13 wt % (based on the isophorone diisocyanate added in the first reactor). The content of the diisocyanate monomers in the product was 0.46 wt %, the color number was 7.5# (Pt—Co color), the product was transparent, and the frequency for cleaning the tail gas pipe was once/4 months.

COMPARATIVE EXAMPLE 1

In the three tank reactors that are connected in series, hexamethylene diisocyanate and water vapour were inlet into the first reactor tank, the temperature of the first reactor was 130-140° C., the flow rate of hexamethylene diisocyanate was 15 kg/h, the catalyst was dibutyl phosphate, the dibutyl phosphate was 0.2 wt % of the mass of the hexamethylene diisocyanate, the feeding rate of the water vapour was 0.3 kg/h, the average residence time of hexamethylene diisocyanate was 30 min, the tail gas of the reactor was cooled and refluxed by circulating water, the temperature of the circulating water was 25-35° C., after condensation, the tail gas entered into a waste liquid tank. The reaction liquid overflew to the second reactor, the average residence time of hexamethylene diisocyanate was 60 min, then the reaction liquid overflew to the third reaction tank, the average residence time of hexamethylene diisocyanate was 160 min. The temperature of the second and the third reaction tanks for producing products were maintained at 140-145° C., the obtained reaction liquid was separated by a two-stage film evaporator to obtain biuret polyisocyanate products, the separation conditions are the same as that of example 1, the color number of the product was 7.5# (Pt—Co color), the content of monomers was 0.17 wt %, the product was white, the loss of hexamethylene diisocyanate was 4.17% (based on the hexamethylene diisocyanate added to the first reactor), and the frequency for cleaning the tail gas pipe was once/1 month.

COMPARATIVE EXAMPLE 2

In the three tank reactors that are connected in series, $H_{12}MDI$ and water vapour were inlet into the first reactor tank, the temperature of the first reactor was 135-140° C., the flow rate of $H_{12}MDI$ solution was 15 kg/h, said solution contains 1 wt % catalyst, propanoic acid, 5 wt% propylene glycol methyl ether acetate, the flow rate of water vapour is 0.27 kg/h, the average residence time of $H_{12}MDI$ in the first reactor is 30 min, the reaction tail gas refluxed directly after being condensed. The reaction liquid overflew to the second reactor, the average residence time of $H_{12}MDI$ was 60 min, then the reaction liquid overflew to the third reaction tank, the average residence time of $H_{12}MDI$ was 170 min. The temperature of the second and the third reaction tanks for producing products were maintained at 135-140° C., the tail gas of the first, second and third reactors were cooled and refluxed by circulating water, the temperature of the circulating water was 25-35° C.; the mixed solution was filtered by 1 μm filter cloth, the reaction liquid obtained by a two-stage separation after filtration was separated by a two-stage film evaporator to obtain biuret polyisocyanate product, the separation conditions are the same as that of example 2. The color number of the obtained product was 17# (Pt—Co color), the product was white, the content of monomers was 0.42 wt %, the loss of $H_{12}MDI$ was 0.21%, the loss of solvent was 3.5%, and the frequency for cleaning the tail gas pipe was once/4 months.

It can be seen that with the method of the present invention, very little amount of polyurea will be generated in the tail gas pipe, and high quality products can still be obtained under longer cleaning cycle. For example, the frequencies for cleaning in examples 1-3 are once/12 months, once/5 months, once/4 months respectively, the color numbers of the prepared products are 5#, 5#, 7.5# respectively, while in comparative example 1, only when the frequency for cleaning is once/1 month, the product of color number 7.5# will be obtained. In comparative example 2, when the adopted frequency for cleaning is the same as that of example 3, the color number is 17#, the product is obviously white.

In addition, with the method of the present invention, the tail gas can return to the reaction mixture after condensation while the quality of the products are still guaranteed, which decrease the loss rate of diisocyanate raw materials and save the materials. For example, the loss rate of diisocyanate in examples 1-3 are all below 0.15%, although the product of color number 7.5# can be obtained in comparative example 1, but the tail gas in the comparative example 1 entered directly into a waste liquid tank after condensation, the loss rate of diisocyanate materials is up to 4.17%; however, the tail gas in comparative example 2 returned to the reaction mixture after condensation, although the loss rate of diisocyanate was low, only 0.21%, but the color number of the product was 17#, the product was white.

Furthermore, from the comparison between the present examples and the comparative examples, when the same kind of diisocyanates was used as raw materials, the content of diisocyanate monomers in the products obtained according to the method of the present invention was low, and the quality of the products obtained according to the method of the present invention was better.

The invention claimed is:
1. A method for continuously preparing biuret polyisocyanate, comprising the following steps:
 a) a mixed solution of a diisocyanate and a catalyst, and water vapour, in an aerosol form, are continuously reacted in a first reactor; wherein the continuous phase of the aerosol is the water vapour, the dispersed phase is the mixed solution of the diisocyanate and the catalyst, and the droplet size of the dispersed phase in the aerosol in step a) is 0.01-50 μm;

b) the product obtained in step a) is brought into a second reactor for a further reaction; a tail gas from the second reactor is condensed and refluxed, and the non-condensable gas is brought into a tail gas treatment system;

c) the reaction liquid obtained in step b) is further reacted in a third reactor; and d) a separation of the reaction liquid obtained in step c) is performed for removing monomers, so as to obtain biuret polyisocyanate.

2. The method according to claim 1, characterized in that: the conversion rate of water vapour in the first reactor is 80-95%, based on the water vapour enter into the first reactor.

3. The method according to claim 2, characterized in that: the total conversion rate of water vapour after step b) is higher than 95%, based on the water vapour enter into the first reactor.

4. The method according to claim 2, characterized in that: the residence time of the aerosol in the first reactor in step a) is 10-60 min.

5. The method according to claim 1, characterized in that: the absolute pressure in the first reactor in step a) is 0.1-1 Mpa, and the temperature is 100-160° C.

6. The method according to claim 1, characterized in that: the molar ratio of diisocyanate and water vapour in step a) is 3:1-15:1.

7. The method according to claim 1, characterized in that: said diisocyanate is one or more of aliphatic diisocyanates, alicyclic diisocyanates and aromatic diisocyanates; said catalyst is a Brnsted acid, and the amount of the catalyst is 0.1-3.0 wt % based on the total amount of diisocyanates.

8. The method according to claim 1, characterized in that: the first reactor is a vertical tubular reactor, a tower reactor or a tank reactor with high height-to-diameter ratio.

9. The method according to claim 1, characterized in that: the average residence time of the reaction liquid in the second reactor in step b) is 20-200 min.

10. The method according claim 9, characterized in that: the temperature of the second reactor in step b) is 120-160° C.

11. The method according to claim 10, characterized in that: said second reactor is a tank reactor or a tower reactor.

12. The method according to claim 1, characterized in that: the temperature of the third reactor in step c) is 130-180° C., and the average residence time is 20-200 min.

13. The method according claim 12, characterized in that: said third reactor is a tubular reactor.

14. The method according to claim 1, wherein the separation for removing monomers in step d) is to separate biuret polyisocyanates from excess diisocyanate monomers through a film evaporator and/or a short-path evaporator, and the content of diisocyanate monomers in the separated biuret polyisocyanate products is less than 0.5 wt %.

15. The method according to claim 2, characterized in that: the conversion rate of water vapour in the first reactor is 85-92%, based on the water vapour enter into the first reactor.

16. The method according to claim 3, characterized in that: the total conversion rate of water vapour after step b) is higher than 99%, based on the water vapour enter into the first reactor.

17. The method according to claim 4, characterized in that: the residence time of the aerosol in the first reactor in step a) is 20-40 min.

18. The method according to claim 1, characterized in that: the droplet size of the dispersed phase in the aerosol in step a) is 0.5-20 μm.

19. The method according to claim 6, characterized in that: the molar ratio of diisocyanate and water vapour in step a) is 5:1-12:1.

20. The method according to claim 1, characterized in that: said catalyst is one or mixtures of more of phosphoric acid, monoalkyl phosphates, dialkyl phosphates, monoaryl phosphates, diaryl phosphates, monocarboxylic acids and dicarboxylic acids.

* * * * *